(12) United States Patent
Virkler et al.

(10) Patent No.: US 8,956,378 B2
(45) Date of Patent: Feb. 17, 2015

(54) COATED EMBOLIZATION DEVICE

(75) Inventors: Joel A. Virkler, Remington, IN (US); Lal Ninan, Santa Rosa, CA (US)

(73) Assignee: Cook Biotech Incorporated, West Lafayette, IN (US)

( * ) Notice: Subject to any disclaimer, the term of this patent is extended or adjusted under 35 U.S.C. 154(b) by 490 days.

(21) Appl. No.: 12/394,823

(22) Filed: Feb. 27, 2009

(65) Prior Publication Data
US 2009/0270978 A1    Oct. 29, 2009

Related U.S. Application Data
(60) Provisional application No. 61/032,789, filed on Feb. 29, 2008.

(51) Int. Cl.
*A61M 29/00*    (2006.01)
*A61L 31/16*    (2006.01)
*A61L 31/10*    (2006.01)

(52) U.S. Cl.
CPC .............. *A61L 31/16* (2013.01); *A61L 31/10* (2013.01); *A61L 2300/236* (2013.01); *A61L 2300/252* (2013.01); *A61L 2300/414* (2013.01); *A61L 2300/45* (2013.01); *A61L 2430/36* (2013.01)
USPC .......................................... 606/191; 606/200

(58) Field of Classification Search
USPC ............................. 606/108, 157, 191, 194, 200
See application file for complete search history.

(56) References Cited

U.S. PATENT DOCUMENTS

| | | | |
|---|---|---|---|
| 2,127,903 A | 3/1938 | Bowen | |
| 2,167,251 A | 7/1939 | Rogers | |
| 3,272,204 A | 9/1966 | Artandi et al. | |
| 4,321,914 A | 3/1982 | Begovac et al. | |
| 4,511,653 A | 4/1985 | Play et al. | |
| 4,781,176 A | 11/1988 | Ravo | |
| 4,801,299 A | 1/1989 | Brendel et al. | |

(Continued)

FOREIGN PATENT DOCUMENTS

| WO | WO 98/22158 | 5/1998 |
|---|---|---|
| WO | WO 98/25637 | 6/1998 |

(Continued)

OTHER PUBLICATIONS

Chapter 2, Scope and Limitations of Solid Electrodes, pp. 19-42.

(Continued)

*Primary Examiner* — David Eastwood
(74) *Attorney, Agent, or Firm* — Woodard Emhardt Moriarty McNett & Henry LLP

(57) ABSTRACT

Described are embolization devices having unique bioactive coatings, as well as methods for their manufacture and use. An illustrative embolization device of the invention comprises an embolic body and a coating material comprising biotropic extracellular matrix material immobilized on a surface of the embolic body. The biotropic extracellular matrix material comprises a network of self-assembled collagen fibrils, and comprises at least one bioactive agent retained in the extracellular matrix material, wherein the bioactive agent is selected from the group consisting of a proteoglycan, a growth factor, a glycoprotein, and a glycosaminoglycan. In certain forms, such an extracellular matrix material comprises a remodelable, angiogenic extracellular matrix material, for example, a submucosa material such as but not limited to porcine small intestinal submucosa.

20 Claims, 3 Drawing Sheets

(56) References Cited

U.S. PATENT DOCUMENTS

| | | | |
|---|---|---|---|
| 4,902,508 A | 2/1990 | Badylak et al. | |
| 4,956,178 A | 9/1990 | Badylak et al. | |
| 4,969,902 A | 11/1990 | Ravo | |
| 5,269,774 A | 12/1993 | Gray | |
| 5,275,826 A | 1/1994 | Badylak et al. | |
| 5,281,422 A | 1/1994 | Badylak et al. | |
| 5,304,123 A | 4/1994 | Atala et al. | |
| 5,411,475 A | 5/1995 | Atala et al. | |
| 5,516,533 A | 5/1996 | Badylak et al. | |
| 5,536,274 A * | 7/1996 | Neuss | 623/1.22 |
| 5,554,389 A | 9/1996 | Badylak et al. | |
| 5,755,791 A | 5/1998 | Whitson et al. | |
| 5,955,110 A | 9/1999 | Patel et al. | |
| 5,983,844 A | 11/1999 | Hauder | |
| 5,997,575 A | 12/1999 | Whitson et al. | |
| 6,099,567 A | 8/2000 | Badylak et al. | |
| 6,117,157 A | 9/2000 | Tekulve | |
| 6,126,686 A | 10/2000 | Badylak et al. | |
| 6,206,931 B1 | 3/2001 | Cook et al. | |
| 6,344,035 B1 * | 2/2002 | Chudzik et al. | 604/265 |
| 6,375,989 B1 | 4/2002 | Badylak et al. | |
| 6,475,232 B1 | 11/2002 | Babbs et al. | |
| 6,589,227 B2 | 7/2003 | Sønderskov Klint | |
| 6,666,892 B2 | 12/2003 | Hiles et al. | |
| 7,025,758 B2 | 4/2006 | Klint | |
| 7,857,825 B2 * | 12/2010 | Moran et al. | 606/200 |
| 2002/0002382 A1* | 1/2002 | Wallace et al. | 606/191 |
| 2002/0082620 A1* | 6/2002 | Lee | 606/151 |
| 2003/0004568 A1* | 1/2003 | Ken et al. | 623/1.46 |
| 2003/0013989 A1 | 1/2003 | Obermiller et al. | |
| 2004/0158185 A1* | 8/2004 | Moran et al. | 602/41 |
| 2005/0004598 A1* | 1/2005 | White et al. | 606/200 |
| 2005/0177103 A1* | 8/2005 | Hunter et al. | 604/96.01 |
| 2005/0187604 A1* | 8/2005 | Eells et al. | 623/1.13 |
| 2006/0058834 A1* | 3/2006 | Do et al. | 606/200 |
| 2006/0206139 A1* | 9/2006 | Tekulve | 606/200 |
| 2007/0225738 A1* | 9/2007 | Pal | 606/151 |

FOREIGN PATENT DOCUMENTS

| | | | | |
|---|---|---|---|---|
| WO | WO 99/47047 A1 | 9/1999 | | |
| WO | WO 9947047 A1 * | 9/1999 | | A61B 17/00 |
| WO | WO 0032112 A1 * | 6/2000 | | A61B 17/12 |
| WO | WO 00/32112 | 8/2002 | | |
| WO | WO 2005/020847 | 3/2005 | | |
| WO | WO 2009/076391 A2 | 6/2009 | | |

OTHER PUBLICATIONS

Heeschen C., et al., "Nicotine stimulates angiogenesis and promotes tumor growth and atherosclerosis," Nature Medicine 7 (2001), No. 7, 833-839.

Johnson, C. et al. "Matrix Matalloproteinase-9 is Required for Adequate Angiogenic Revascularization of Ischemic Tissues—Potential Role in Capillary Branching", Circulation Research (2004) 94;262-268. American Heart AssociatiOn, Dallas, TX.

* cited by examiner

COATED EMBOLIZATION DEVICE

CROSS-REFERENCE TO RELATED APPLICATIONS

This application claims the benefit of U.S. Provisional Patent Application Ser. No. 61/032,789, filed Feb. 29, 2008, which is hereby incorporated by reference.

BACKGROUND

The present invention relates generally to medical devices and in particular aspects to embolization devices.

As further background, during the diagnosis, treatment, and follow-up of various medical conditions, it may be necessary or desirable for a physician to occlude a passageway or other open space within a patient's body. For example, a physician may need to block a particular blood vessel, deprive a certain area of life-sustaining blood, or fill a cavernous area in a blood vessel. In situations where a blood vessel is perforated, blood can flow out of the vessel and into surrounding areas causing a hemorrhage. For this condition, the physician will need to, inter alia, plug the perforation and/or occlude the vessel upstream of the perforation. In another example, where a tumor is discovered, one therapy for reducing the tumor or eliminating it completely is to occlude the vessel upstream of the tumor. In some instances, the blood-deprived tumor will die off. In both of these examples, a strategically placed thrombus or embolism completes the desired occlusion.

In the case of aneurysm treatment, an aneurysm is caused by a weakening of the vessel wall, which causes an invagination of the vessel wall. Blood flow is inhibited at the neck of the aneurysm due to turbulence caused by blood entering and exiting the lumen of the aneurysm. An aneurysm in the brain, especially one that has ruptured, can have catastrophic consequences including but not limited to subarachnoid hemorrhage, stroke, permanent neurological deficits, and death.

Surgical procedures to treat aneurysms, e.g., aneurysm "clipping," can be extremely risky, and in some cases, impossible depending on the anatomical location of the aneurysm. As an alternative to surgery, a number of minimally invasive procedures have been developed whereby both ruptured and unruptured aneurysms can be treated using embolization devices. Such devices can include aneurysm coils, injectable "fillers," and various other implants. In some instances, one or more embolization devices are delivered to an aneurysm treatment site using a catheter (and possibly a guide-wire) that is advanced from the groin to the treatment site. An embolization device is then inserted through the catheter and into the aneurysm. Such a procedure can be repeated until enough devices are "packed" into the aneurysm sac to fill it.

A common treatment method for cerebral aneurysms involves the implantation of metallic embolization coils into the lumen of the aneurysm. One such coil is the FDA approved Gugliemi Detachable Coil. However, this platinum coil has limited thrombus promoting characteristics and typically does not provide a complete packing of the aneurysm lumen. It is not uncommon for an aneurysm treated with such a device to re-canalize, enlarge, and even rupture. Therefore, an aneurysm lumen filling device that suitably packs the lumen, is configured to reduce the chance of device migration following implantation, is biocompatible, and promotes healing of the aneurysm would be well-received as, by one estimate, approximately 28,000 patients suffer from intracranial aneurysms, of which 19,000 become severely disabled or die as a result of an aneurysm rupture.

There remain needs for improved and/or alternative embolization devices, as well as methods for manufacturing and using such devices. The present invention is addressed to those needs.

SUMMARY

The present invention provides, in certain aspects, embolization devices having unique bioactive coatings. For example, an illustrative embolization device of the invention comprises an embolic body and a coating material immobilized on a surface of the embolic body. The coating material comprises a biotropic extracellular matrix (ECM) material comprising a network of self-assembled collagen fibrils and at least one bioactive agent retained in the ECM material. The bioactive agent is selected from the group consisting of a proteoglycan, a growth factor, a glycoprotein, and a glycosaminoglycan. Such an embolization device, alone or in conjunction with one or more other suitable devices, can be used to occlude, or at least promote and/or facilitate occlusion of, a lumen or other open space within a patient's body. The coating material may coat the entire surface of the embolic body, or any portion thereof, and may comprise one or more individual ECM material layers. In some embodiments, the ECM material comprises a remodelable, angiogenic ECM material, for example, a submucosa material such as but not limited to porcine small intestinal submucosa. The embolic body can exhibit any suitable size, shape, and configuration, and can be formed with one or more of a variety of biocompatible materials. In certain forms, the embolic body comprises a platinum coil.

In one particular embodiment, the invention provides a method of forming a coated embolization device. This method comprises (i) providing an embolic body; (ii) coating a surface of the embolic body with a flowable biotropic ECM material, wherein the biotropic ECM material includes at least one retained bioactive agent, the bioactive agent being selected from the group consisting of a proteoglycan, a growth factor, a glycoprotein, and a glycosaminoglycan; and (iii) reconstituting the flowable biotropic ECM material to provide an immobilized layer of ECM material on the embolic body surface, wherein the immobilized layer of ECM material has a network of self-assembled collagen fibrils and entrains the at least one bioactive agent. Immobilization of the ECM material coating can be accomplished in any suitable manner. In certain aspects, an ECM gel coating layer is caused or allowed to reconstitute or otherwise reassemble by being subjected to suitable air drying conditions.

In another embodiment, the present invention provides a medical product, which includes an embolization device such as that described above enclosed within a sealed package. In some forms, the package includes indicia identifying the contents of said package for use in treating an aneurysm.

The present invention also provides, in one aspect, a method of occluding a space within a bodily vessel. This method comprises delivering to the space an embolization device such as that described above. In certain embodiments, such a method comprises delivering one or more coated embolization devices of the invention to a vascular treatment site (e.g., into an aneurismal sac and/or into the neck of an aneurysm) using a suitable delivery device, for example, a translumenally advancable device such as but not limited to a catheter.

In another aspect, the present invention provides a method of forming a coated embolization device. This method comprises (i) providing an embolic body; and (ii) immobilizing a coating material on a surface of the embolic body. Such a coating material comprises a biotropic extracellular matrix material, wherein the biotropic extracellular matrix material has a network of self-assembled collagen fibrils and at least one retained bioactive agent. The bioactive agent is selected from the group consisting of a proteoglycan, a growth factor, a glycoprotein, and a glycosaminoglycan.

In another embodiment, the invention provides a method of forming a coated embolization device. This method comprises the steps of: (i) providing an embolic body; (ii) coating a surface of the embolic body with a flowable biotropic extracellular matrix material, wherein the biotropic extracellular matrix material comprises at least one retained bioactive agent, the bioactive agent being selected from the group consisting of a proteoglycan, a growth factor, a glycoprotein, and a glycosaminoglycan; and (iii) subjecting the flowable extracellular matrix coating to conditions effective to form a solidified extracellular matrix coating immobilized on the embolic body surface, wherein the solidified extracellular matrix coating entrains the at least one bioactive agent.

Other objects, embodiments, forms, features, advantages, aspects, and benefits of the present invention shall become apparent from the detailed description and drawings included herein.

DETAILED DESCRIPTION

Figure 1:
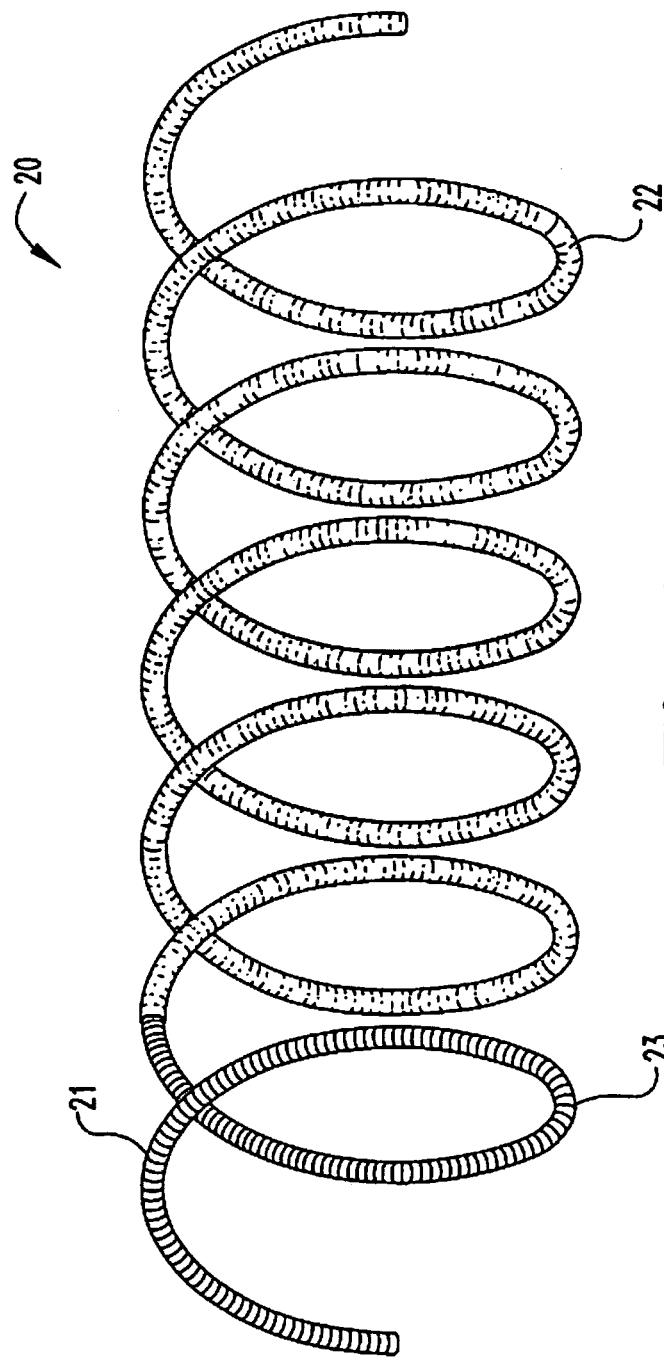
FIG. 1 is a perspective view of a coated embolization device according to one embodiment of the invention.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, in certain aspects, the present invention provides embolization devices having unique bioactive coatings. For example, an illustrative embolization device of the invention comprises an embolic body and a coating material immobilized on a surface of the embolic body. The coating material comprises a biotropic ECM material that includes a network of self-assembled collagen fibrils and at least one bioactive agent retained in the ECM material. The bioactive agent is selected from the group consisting of a proteoglycan, a growth factor, a glycoprotein, and a glycosaminoglycan. Such an embolization device, alone or in conjunction with one or more other suitable devices, can be used to occlude, or at least promote and/or facilitate occlusion of, a lumen or other open space within a patient's body. The coating material may coat the entire surface of the embolic body, or any portion thereof, and may comprise one or more individually formed ECM material layers. In certain preferred aspects, the ECM material comprises a remodelable, angiogenic ECM material, for example, a submucosa material such as but not limited to porcine small intestinal submucosa. The embolic body can exhibit any suitable size, shape, and configuration, and can be formed with one or more of a variety of biocompatible materials. In certain forms, the embolic body comprises a platinum coil. The invention also provides methods of forming and utilizing such embolization devices, as well as medical products that include such devices enclosed within sterile packaging.

With reference now to FIG. 1, shown is a perspective view of an illustrative embolization device 20 of the invention. The embolization device 20 includes an embolic body 21 and a coating material 22 comprising a reconstituted biotropic ECM material immobilized on a surface of the embolic body 21. The embolic body 21, which has an overall shape of a helical coil, is formed with a biocompatible, metallic material such as platinum. As discussed more thoroughly below, such an overall helical coil shape can be formed by winding a length of platinum wire into a primary coil, and then winding the primary coil into a secondary (helical) coil. Also, a coating material such as that shown in FIG. 1 may be applied before and/or after formation of the primary and/or secondary coil, and may or may not coat the entire surface of the embolic body. In this particular embodiment, the embolic body 21 is shown having an uncoated portion 23 for illustrative purposes.

The coated embolization devices described herein have a thrombogenicity and/or an occlusion inducing, promoting, and/or facilitating quality. In this regard, embolization device 20 and other coated devices of the invention can be used alone or in conjunction with one or more other suitable devices to occlude, or at least promote and/or facilitate occlusion of, a lumen or other open space within a patient's body. For example, the coated embolization device 20 can be used to induce thrombus formation in an aneurismal sac, which can lead to endothelialization across the aneurysm neck. In certain forms of the invention, such occlusive qualities are enhanced by selecting coating materials that are receptive to tissue ingrowth, and in some cases, selecting coating materials that induce and/or promote patient cells to grow into the coating material. Remodelable coating materials may be used in this context to promote cellular growth within the coating material, which can, inter alia, help to anchor the device at the implantation site and provide occlusion.

Immobilization of the coating material 22 on the embolic body surface can be accomplished in any suitable manner. In preferred aspects of the invention, this comprises disposing on the surface an amount of a flowable ECM material and thereafter causing or allowing the ECM material to reconstitute or otherwise reassemble, for example, by subjecting it to suitable air drying conditions. The reassembled ECM material has a network of self-assembled collagen fibrils, and comprises at least one bioactive agent retained in the ECM material, the bioactive agent being selected from the group consisting of a proteoglycan, a growth factor, a glycoprotein, and a glycosaminoglycan.

In accordance with the present invention, an ECM coating material can become immobilized on an embolic body surface, at least due in part, to chemical bonds formed within the ECM material (e.g., within and/or between certain components of the ECM material) during a reconstitution or other reassembly process and/or chemical bonds formed between components of the ECM material and the embolic body surface. Illustratively, an aldehyde group formed on a first ECM component of an ECM starting material can be caused or allowed to react to crosslink that ECM component to itself or another ECM component of the ECM starting material (e.g., to crosslink two collagen molecules, two non-collagen molecules, or a collagen molecule with a non-collagen molecule) through an imine bond (commonly referred to as a Schiff's base link) formed between the aldehyde of the first ECM component and an amine (lysine amino acid residue) on the same component or on another ECM component. Illustratively, such an amine can be provided by arginine, asparagine, glutamine, and lysine. As well, an aldehyde group occurring on a component of the ECM starting material can be caused or allowed to form a bond with an amine group on the surface of the embolic body.

The size, shape, and configuration of the embolization device 20 can vary. In some forms, coated devices of the invention are advantageously adapted to fit within the lumen of a suitable delivery device, either in a relaxed or unrelaxed condition, and then upon being deployed at the treatment site (e.g., within a lumen or other open space in the vasculature of an animal, especially a human), to remain there and provide treatment to the patient. Suitable delivery devices include but are not limited to cannulated, translumenally advanceable devices. In certain aspects, one or more devices such as device 20 are delivered to a treatment site, e.g., into an aneurysm sac and/or the neck of an aneurysm, using a catheter.

While the embolic body depicted in FIG. 1 is formed with a biocompatible, metallic material, it should be noted that suitable embolic bodies can be formed with one or more of a variety of materials. These materials may be rigid, malleable, semi-flexible, or flexible. The material(s) selected for a particular embolic body can depend on a number of factors including but not limited to the intended use of the embolization device, as well as its size, shape, and configuration. In general, suitable material(s) will be selected to allow a coated product of the invention to have certain desired performance and other characteristics, for example, to exhibit a flexibility falling within a desired range and/or to have shape memory.

Suitable biocompatible metallic materials that can be used in some forms of the invention include but are not limited to gold, rhenium, platinum, palladium, rhodium, ruthenium, various stainless steels, tungsten, titanium, nickel, cobalt, tantalum, iron, and copper, as well as alloys of these and other suitable metals, e.g., cobalt alloys, such as Elgiloy®, a cobalt-chromium-nickel alloy, MP35N, a nickel-cobalt-chromium-molybdenum alloy, and a nickel-titanium alloy, e.g., Nitinol®. In certain preferred aspects, an alloy is selected that exhibits excellent biocompatibility and yet has suitable strength and ductility to be wound into coils of primary, and potentially also secondary shape, and will retain any such shapes upon placement of the embolization device in the body, particularly the human body. Additionally or alternatively, embolic bodies can include material in the form of yarns, fibers, and/or resins, e.g., monofilament yarns, high tenacity polyester, and the like, as well as other plastic, resin, polymer, woven, and fabric surgical materials, other conventional synthetic surgical materials, such as shape-memory plastics, and combinations of such materials. Further, one or more suitable ceramic materials including but not limited to hydroxyapatite, alumina and/or pyrolytic carbon can be used to form all or part of an embolic body.

Synthetic polymeric materials that can be used to form all or part of an embolic body include but are not limited to bioresorbable and non-bioresorbable plastics. Suitable bioresorbable, or bioabsorbable polymers include but are not limited to poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyhydroxyalkanaates, polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, and polyphosphazenes. These or other bioresorbable materials may be used, for example, where only a temporary blocking or closure function is desired, and/or in combination with non-bioresorbable materials where only a temporary participation by the bioresorable material is desired.

Suitable non-bioresorbable, or biostable polymers include but are not limited to polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate.

While the embolic body depicted in FIG. 1 is generally in the shape of a helical coil, it should be understood that suitable embolic bodies can exhibit a variety of shapes. Advantageously, the shape selected will allow the device, by itself or in conjunction with one or more other suitable devices, to occlude, or at least promote and/or facilitate occlusion of, a space within a patient's body. Examples of suitable embolic bodies include but are not limited to, vascular occlusive devices including vaso-occlusive coils and microcoils, vascular wires, injectable embolic devices, embolic implants, embolic plugs, expandable implants, vascular plugs, embolic vascular endoprostheses, and embolic microspheres, of any suitable size, shape, and configuration. Further, prior to be coated, any of these embolic bodies (or any other suitable embolic body) can be coupled to or otherwise associated with one or more additionally thrombogenic components such as but not limited to strands, filaments, fibers including bundled fibers, windings, coils, particles, twisted elements, and/or meshes, whether such components are already coated or uncoated. As well, such additionally thrombogenic components can be incorporated into an embolic device during and/or after the application of any coating layer to the device in accordance with the invention.

A helical coil such as the one depicted in FIG. 1 may be constructed in any suitable manner and using any suitable equipment. Illustratively, a helical coil may be prepared by wrapping a suitable wire about a cylindrical or conical mandrel. In so doing, advantageously coil implants will be suitably configured to avoid substantially cutting, tearing, and/or causing other trauma to any surrounding soft tissues upon placement of the coils in the patient. Accordingly, any loose end of a helical wire coil may be placed axially through the core of the helix and/or such a wire end may be suitably bound to another part of the device, e.g., by heat, adhesives, and/or mechanical means. Further, any additional thrombogenic elements (e.g., particles, radial filaments, etc.) may be attached to portions of the coil by these and/or other suitable binding techniques, e.g., by tying or otherwise adhering them to the coil.

Embolization devices which take the form of coils include but are not limited to helically wound coils, random wound coils, coils wound within coils, and other suitable coil configurations. Such coils are generally formed with radiopaque metallic materials such as but not limited to those listed above. In some instances, several coils are placed at a given location within the vasculature, for example, within a vessel or within a space associated with a vessel such as an aneurysm sac, to more completely occlude, and in some cases, substantially or completely occlude, the flow of blood through the vessel or other space associated with the vessel. Thrombus formation on and around the coils further enhances the occlusive effect of the coils.

Advantageous coated embolization devices of the invention are configured to resist unacceptable migration from the treatment site following implantation. Initially, device migration is inhibited, at least in part, by contact with tissues and/or other devices or materials at the implantation site, and then, after a period of time, the growth of new patent tissue (e.g., thrombus formation) into, on, and/or around the implanted device helps anchor the device. Illustratively, a coated device of the invention can be deigned to conform to surrounding tissues at the implantation site and/or its design can take into account the type of tissue and the geometry at the implantation site and the ability of the implantation site tissues to conform around the device.

Although not necessary to broader aspects of the invention, in some embodiments, an embolization device is configured to cause an acceptable amount of trauma to tissues at the treatment site upon deployment, which can serve to initiate a localized healing response effective to enhance the growth of new patient tissue at the treatment site. Additionally, certain inventive coated devices can be configured to embed within tissue at the implantation site, e.g., soft tissues surrounding an aneurysm sac, to inhibit the device from migrating from the site. However, any device capable of causing such traumas should be configured so as to not undesirably damage tissues at the treatment site (e.g., cause a hemorrhage by puncturing an aneurysm sac).

Certain preferred embolic bodies have a degree of flexibility. For example, an embolic coil useful in some forms of the invention is formed with an elastic material that allows it to generally resume its original (relaxed) shape after being stretched or compressed. Of course, in some instances, such an elastic coil when used in a coated embolization device of the invention will be prevented from resuming its original shape upon deployment due to contact with other objects at the treatment site (e.g., patient tissues lining an aneurysm or other embolization devices packed into the aneurysm).

In some embodiments, an embolic coil is formed with an elastic material that allows it to attain a first, stretched configuration and a second, relaxed configuration. Illustratively, a helical coil can exhibit a generally linear, helical configuration when stretched and a comparatively compact, convoluted configuration when relaxed. This stretched configuration can be advantageous in some forms of the invention, for example, when a catheter having a particularly small diameter is needed to place the coil at the treatment site. Upon deployment from the catheter lumen and into the treatment site, such a coil can be allowed or caused to assume a relaxed configuration, which can enhance the occlusive characteristics of the emplaced coil.

Wire, when used in making an embolic body useful in some forms of the invention, can be of any suitable size, shape, and configuration, and can be formed with any suitable material(s). Since immobilizing a coating material on a surface of an embolic wire can alter certain performance or other characteristics of the embolic wire, in accordance with the invention, a wire type can be selected to modulate one or more characteristics of the coated wire, for example, to provide a coated wire having a flexibility within a predetermined range. Of course, as discussed more thoroughly elsewhere herein, other factors such as but not limited to the type of coating material(s) selected, the number of coating layers applied, and the coating technique(s) utilized, can affect the performance and other characteristics of the coated device, and in this regard, different combinations of such factors can be developed through routine experimentation so as to provide a coated embolization device having suitable characteristics for a particular application.

The diameter of a piece of wire may or may not be constant along its length, and in certain aspects, is in the range of about 0.002 inches to about 0.100 inches, more typically in the range of about 0.005 to about 0.050 inches. In some forms, a suitable embolization coil has a primary coil, and potentially also a secondary coil. Such a primary coil can have a primary coil diameter, in a relaxed configuration, in the range of about 0.007 inches to about 0.120 inches, more typically from about 0.010 inches to about 0.030 inches. As well, the axial length of such an embolization coil, in a relaxed configuration, may vary, and is typically in the range of about 0.20 inches to about 50 inches, more typically from about 0.20 inches to about 40 inches. Such an embolic coil is typically wound to have between 2 and 100 turns per centimeter.

In one embodiment, an embolic coil is formed with wire having a diameter in the range of about 0.01 mm to about 0.1 mm, more typically from about 0.02 mm to about 0.05 mm. Such a coil can have a primary coil, and potentially also a secondary coil, wherein the primary coil diameter, in a relaxed configuration, is typically in the range of about 0.03 mm to about 0.140 mm, more typically in the range of about 0.05 mm to about 0.030 mm. As well, the axial length of the coil, in a relaxed configuration, may vary, and is typically in the range of about 30 cm to about 1000 cm, more typically from about 90 cm to about 300 cm. In certain aspects, the embolic coil is expandable so that in an unexpanded configuration, the wire is formed into a tightly-wound coil, having a diameter in the range of about 0.1 mm to about 1 mm, more typically from about 0.25 mm to about 0.5 mm, and a length in the range of about 2 mm to about 60 cm, more typically from about 25 mm to about 15 cm. The coil will typically have from about 20 turns to about 60,000 turns, more typically from about 1000 turns to about 6000 turns. In an expanded configuration (e.g., upon deployment), the wire forms a random structure larger in all dimensions than the initial, unexpanded coil, which can enhance the occlusive characteristics of the deployed coil.

Turning now to a general discussion of device coatings and coating processes useful in the present invention, it should again be noted that a device coating of the invention may be comprised of one or more individual material layers. Also, any material layer added to a device may or may not coat the entire surface of the device, whether the to-be-coated device is uncoated or already fully or partially coated. Additionally, for embolization devices that are capable of achieving one or more configurations (e.g., a primary and a secondary coil configuration as shown in FIG. 1), one or more coating layers may be added to the device before and/or after the device is placed into any such configuration. Illustratively, in some forms, a generally straight piece of wire is subjected to a coating process in accordance with the present invention, and then the coated wire is suitably formed into a coil. This coil may then be subjected to another coating process and/or formed into a secondary coil. In other forms, a piece of wire is suitably formed into a coil, and then the coil is subjected to a coating process of the invention. This coil may then be formed into a secondary coil and optionally re-coated. The coated embolization coil depicted in FIG. 1 can be formed by any suitable method.

Nonetheless, when subjecting a coated device of the invention to further processing (e.g., to further structural or other manipulation), care should be taken to not adversely affect the desired physical, biological, or other characteristics of the coated embolization product being formed. Illustratively, when coiling a coated piece of wire, for example as described above, care should be taken to cause as little delamination as possible of the coating from the device surface. As well, because certain processing steps can destroy the remodelable properties of a remodelable material (e.g., subjecting the coated device to certain elevated temperatures), where preservation of remodelable properties is desired, any further processing of a coated device can be performed to an extent or in a fashion that allows the material to retain at least a portion of its remodelable properties.

The number of coating layers selected for a particular device of the invention can be used to modulate one or more properties of the coated product, such as but not limited to, its flexibility, overall coating thickness, surface morphology, and/or durability characteristics including resistance to coating material delamination during product handling and delivery. In this regard, while the coating material depicted in FIG. 1 comprises a single layer of material, it should be understood that coating materials of the invention can comprise any suitable number of layers of material. Depending at least on the characteristics of the flowable ECM starting material (and other potential factors including but not limited to the process used to form the any individual coating layer, etc.), one to twenty or more individual coating layers may be applied to an embolic body in accordance with the present invention. Illustratively, a platinum coil having a primary coil diameter of about 250 µm to about 500 µm, in certain aspects, will typically have an overall coating thickness in accordance with the present invention of about 0.5 µm to about 20 µm, more typically from about 0.5 µm to about 10 µm.

Figure 2A:
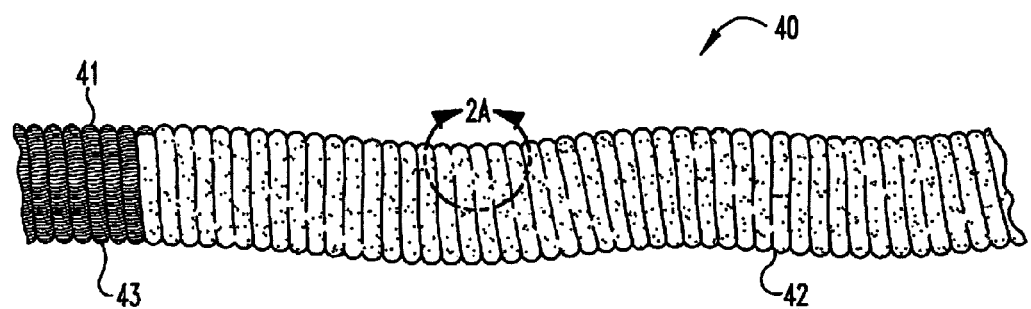
FIG. 2A is a partial, side view of another coated embolization device of the invention.

With reference now to FIG. 2A, shown is a perspective view of another illustrative embolization device 40 of the invention. The embolization device 40 includes an embolic body 41 and a coating material 42 comprising a reconstituted or otherwise reassembled biotropic ECM material immobilized on a surface of the embolic body 41. The embolic body 41, which is in the form of a tightly wound yet flexible coil, is formed with a biocompatible, synthetic material, although the embolic body 41 may be comprised of any suitable biocompatible material such as platinum. Such a coil can be formed by taking a piece of malleable wire and wrapping it around a mandrel or other suitable device, for example, as described elsewhere herein. In some embodiments, such a length of coil is considered a primary coil, which can be further processed, for example, by being formed into a secondary coil similar to that shown in FIG. 1. In this embodiment, the embolic body 41 is shown having an uncoated portion 43 for illustrative purposes.

The coating material 42 may comprise one or more individual material layers, wherein such layer(s) can be immobilized on the device before and/or after the coil is formed. In some forms, the coil is formed and subsequently coated. Depending on factors such as but not limited to the properties of the ECM starting material, the configuration of the embolic body, and the processing method utilized, the coating material may or may not coat the entire surface of the synthetic, malleable wire forming the embolic body. In this regard, such a coating material, in certain aspects, is able to flow around each individual turn of the coil during a coating process so as to coat the entire surface of the wire. In other aspects, such a coating material coats less than the entire surface of the wire. Illustratively, the coating material may additionally or alternatively provide a sheath or sheath-like coating that surrounds and covers the overall coil body, e.g., coating only the outer surfaces of a primary coil.

Figure 2B:
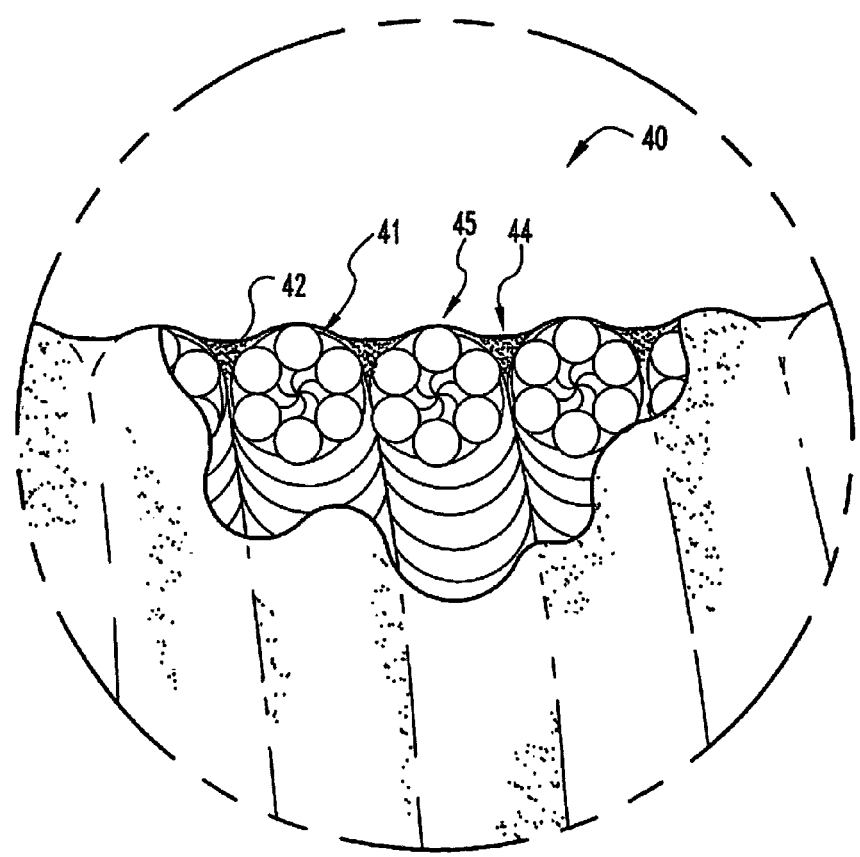
FIG. 2B is a partial, enlarged view of the device of FIG. 2A.
Figure 3A:
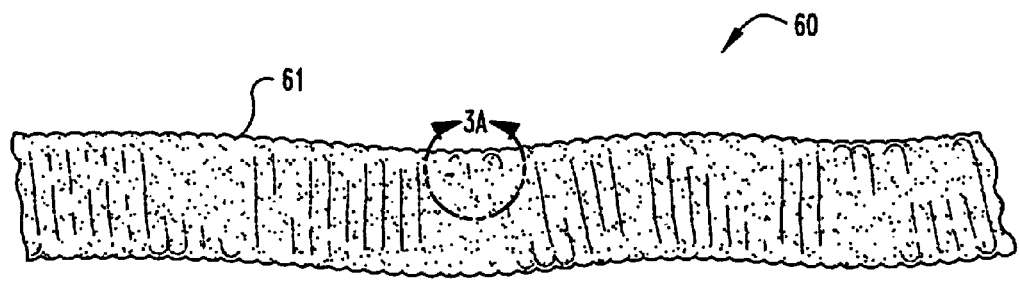
FIG. 3A is a partial, side view of another coated embolization device of the invention.
Figure 3B:
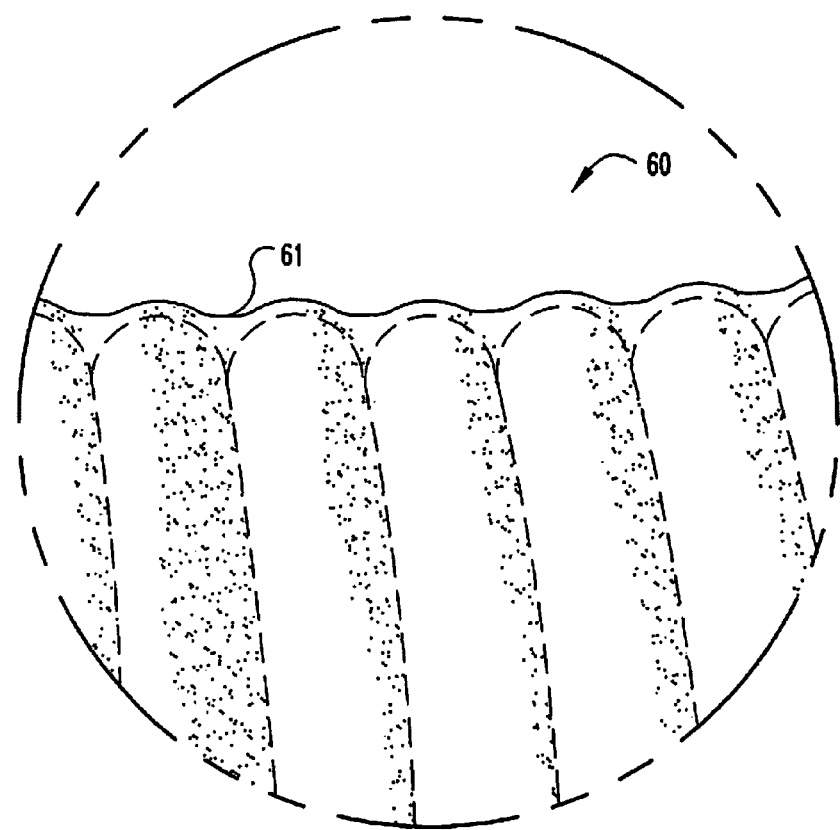
FIG. 3B is a partial, enlarged view of the device of FIG. 3A.

Further in this regard, an ECM coating material of the invention need not uniformly coat the embolic body surfaces which it coats. In accordance with certain aspects of the present invention, for example as shown in FIGS. 2A and 2B, relatively more ECM material may accumulate and become immobilized and/or stabilized in spaces 44 between individual turns of the coil compared to other spaces surrounding the coil turns, e.g., those adjacent to the top, outer surfaces 45 of the turns. In some forms, the viscosity of the ECM starting material can affect the characteristics of the coating layer that is later formed, for example, the uniformity and thickness of the coating material between and around individual turns of the coil. FIGS. 3A and 3B show a coated embolization device 60, which is similar to that of FIG. 2A, except that it has a relatively thicker coating material 61 immobilized on a surface of the embolic body. Increasing the thickness of an overall coating material can be accomplished in any suitable manner. In some aspects, this is accomplished by using an ECM starting material having a relatively higher viscosity. In other aspects, increasing the thickness of an overall coating is accomplished by increasing the number of individual coating layers added to the device.

Coating materials useful in the invention should generally be biocompatible, and in advantageous embodiments of the invention, the coating materials are comprised of a remodelable material. Particular advantage can be provided by coating materials including a remodelable collagenous material. Such remodelable collagenous materials can be provided, for example, by collagenous materials isolated from a warm-blooded vertebrate, for example, a mammal such as a pig or a human. Such isolated collagenous material can be processed so as to have remodelable, angiogenic properties and promote cellular invasion and ingrowth. Remodelable materials may be used in this context to promote cellular growth within sites in which coated embolic products of the invention are implanted.

Suitable remodelable materials can be provided by collagenous extracellular matrix (ECM) materials possessing biotropic properties. For example, suitable collagenous materials include ECM materials such as submucosa, renal capsule membrane, amnion, dura mater, pericardium, serosa, peritoneum and basement membrane layers, including liver basement membrane and epithelial basement membrane materials, and whether isolated from juvenile or adult animal sources. Suitable submucosa materials for these purposes include, for instance, small intestinal submucosa, stomach submucosa, urinary bladder submucosa, and uterine submucosa. Submucosa useful in the present invention can be obtained by harvesting such tissue sources and delaminating the submucosa from smooth muscle layers, mucosal layers, and/or other layers occurring in the tissue source. For additional information as to submucosa useful in the present invention, and its isolation and treatment, reference can be made, for example, to U.S. Pat. Nos. 4,902,508, 5,554,389, 5,993,844, 6,206,931, and 6,099,567. Renal capsule membrane can also be obtained from warm-blooded vertebrates, as described more particularly in International Patent Application serial No. PCT/US02/20499 filed Jun. 28, 2002, published Jan. 9, 2003, as WO03002165.

Submucosa tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the present invention.

ECM coating materials may include one or more bioactive agents native to the tissue source of the materials. For example, a submucosa or other remodelable ECM tissue material useful in some forms of the invention may retain one or more growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bioactive components such as but not limited to proteins, glycoproteins, proteoglycans, and glycosaminoglycans. For example, an ECM material may retain heparin, heparin sulfate, hyaluronic acid, fibronectin, cytokines, and the like. Thus, generally speaking, a submucosa or other ECM material may retain one or more bioactive components that induce, directly or indirectly, a cellular response such as a change in cell morphology, proliferation, growth, protein or gene expression.

Further, in addition or as an alternative to the inclusion of such native bioactive components, non-native bioactive components such as those synthetically produced by recombinant technology or other methods (e.g., genetic material such as DNA), may be incorporated into an ECM material before, during, and/or after a coating layer is immobilized. These non-native bioactive components may be naturally-derived or recombinantly produced proteins that correspond to those natively occurring in an ECM tissue, but perhaps of a different species (e.g., human proteins applied to collagenous ECMs from other animals, such as pigs). Suitable non-native bioactive components useful in some forms of the invention may include one or more drug substances. Illustrative drug substances that may be added to an ECM material include, for example, antibiotics, anti-inflammatory agents, and anti-proliferative agents, e.g. taxol derivatives such as paclitaxel. Such non-native bioactive components can be incorporated into and/or onto the ECM material in any suitable manner. For example, in some forms, a bioactive agent is mixed with a suitable flowable ECM starting material before a solidified coating is formed, and thus is incorporated into the immobilized coating. In other forms, a bioactive agent is incorporated into an already-formed device coating in a suitable manner such as but not limited to by surface treatment (e.g., spraying) and/or impregnation (e.g., soaking).

Suitable coating materials can include xenograft material (i.e., cross-species material, such as tissue material from a non-human donor to a human recipient), allograft material (i.e., interspecies material, with tissue material from a donor of the same species as the recipient), and/or autograft material (i.e., where the donor and the recipient are the same individual). For example, in certain aspects of the invention, a coating material includes ECM material, wherein the ECM material is xenogenic relative to the patient receiving the embolic implant, and any added exogenous material(s) are from the same species (e.g. autologous or allogenic) as the patient receiving the embolic implant. Illustratively, human patients may be treated with products including an xenogenic ECM material (e.g. porcine-, bovine- or ovine-derived material) that has been modified with exogenous human material(s) as described herein, those exogenous materials being naturally derived and/or recombinantly produced.

Turning now to a general discussion of methods of the invention for forming coated embolization devices, in certain aspects, upon selection of a suitable embolic body and a suitable coating layer starting material such as any of those described herein (e.g., a flowable collagenous ECM material), the surface of the embolic body, or any portion thereof, is coated with an amount of the starting material. (As described in detail below, in some forms of the invention, the surface of the embolic body, or any portion thereof, can be subjected to some form of pre-treatment to promote, facilitate, and/or otherwise enhance the coating process, although it must be understood that any form of pre-treatment is optional.) The stating material can be disposed on the embolic body surface in any suitable manner including but not limited to by dipping the embolic body into the starting material one or more times. Thereafter, the flowable ECM material is caused or allowed to reconstitute or otherwise reassemble to form a collagenous material layer immobilized on the embolic body surface. In certain preferred aspects of the invention, the coating material comprises hydrolyzed collagenous ECM material including at least one retained bioactive agent, wherein the bioactive agent is selected from the group consisting of a proteoglycan, a growth factor, a glycoprotein, and a glycosaminoglycan. In this context, reconstitution of the ECM material provides a network of self-assembled collagen fibrils, and entrains the at least one bioactive agent in the ECM material.

Suitable coating layer starting materials come in many different forms. In certain preferred aspects, such starting materials include flowable or otherwise conformable collagenous ECM materials that are at least partially solubilized or otherwise denatured or disassembled relative to their native collagenous structures. Illustratively, a suitable conformable ECM material may comprise an ECM material paste, a fluidized ECM material, and/or gelatinous ECM material. In some forms, an ECM graft material comprises a flowable composition comprising solubilized or suspended ECM material such as an ECM hydrolysate material. Suitable flowable, remodelable ECM materials for use in this aspect of the invention can be prepared, for example, as described in U.S. Pat. Nos. 5,275,826, 5,516,533, 6,206,931, and/or 6,444,229 or in International Publication No. WO2005020847 (Cook Biotech Incorporated) published Mar. 10, 2005, which are each hereby incorporated by reference in their entirety.

In accordance with one aspect of the invention, a flowable ECM composition will exhibit the capacity to reassemble or otherwise solidify upon adjusting the pH of a relatively more acidic aqueous medium containing it to about 5 to about 9, more preferably about 6.6 to about 8.0, and typically about 7.2 to about 7.8, thus inducing fibrillogenesis and matrix assembly. In one embodiment, the pH of a flowable ECM material can be adjusted by the addition of a buffer that does not leave a toxic residue, and has a physiological ion concentration and the capacity to hold physiological pH. Examples of suitable buffers include PBS, HEPES, and DMEM. Illustratively, the pH of a flowable ECM material can be raised by the addition of a buffered NaOH solution to 6.6 to 8.0, more preferably 7.2 to 7.8, to promote and/or facilitate the formation of an ECM-containing coating layer. Any suitable concentration of NaOH solution can be used for these purposes, for example, including about 0.05 M to about 0.5 M NaOH. In accordance with an embodiment, the flowable ECM material is mixed with a buffer, and sufficient 0.25 N NaOH is added to the mixture to achieve the desired pH. If desired at this point, the resultant mixture can be applied to a device and incubated at 37° C. for 0.5 to 1.5 hours to form an immobilized ECM coating layer.

Flowable or otherwise conformable ECM materials useful in some forms of the invention can be prepared to have desirable properties for handling and use. For example, a fluidized ECM hydrolysate can be prepared in an aqueous medium, which can thereafter be caused or allowed to form a gel for use in the invention. Such prepared aqueous mediums can have any suitable level of ECM hydrolysate therein. Typically, the ECM hydrolysate will be present in the aqueous medium at a concentration of about 2 mg/ml to about 200 mg/ml, more typically about 8 mg/ml to about 120 mg/ml, and in some embodiments about 10 mg/ml to about 75 mg/ml. In certain illustrative forms, the aqueous ECM hydrolysate composition to be gelled will have an injectable character, for example, by injection through a needle having a size in the range of 18 to 31 gauge (internal diameters of about 0.047 inches to about 0.004 inches). Further, flowable ECM compositions can be prepared so that in addition to neutralization, heating to physiologic temperatures (such as 37° C.) will substantially reduce the time needed to solidify or otherwise immobilize the ECM material on the embolic device surface.

It should be noted that the ionic strength of a solubilized or otherwise flowable ECM material is believed to be important in maintaining the fibers of collagen in a state that allows for fibrillogenesis and matrix assembly upon neutralization of the solubilized ECM in certain forms of the invention, and accordingly, if needed, the salt concentration of the flowable ECM material can be reduced prior to a reconstitution or other coating layer assembly step. Also, the flowable ECM material can be reconstituted or otherwise reassembled to form a coating layer at any suitable temperature, e.g., ranging from about 4° C. to about 40° C. The temperature will typically affect the immobilization times, which may, in certain embodiments, range from about 5 to about 120 minutes at the higher reassembly temperatures and about 1 to about 8 hours at the lower reassembly temperatures.

Continuing now with a general discussion of methods of the invention for forming a coated embolization device, it should be noted that a flowable or otherwise conformable collagenous surface coating material can be reconstituted or otherwise reassembled in any suitable manner. Illustratively, an immobilized layer of collagenous material can be formed on a surface of an embolization device by suitably placing on the surface a flowable collagenous material, and then allowing the flowable material to dry. For example, in certain aspects, an embolic coil is at least partially dipped in a bath containing flowable submucosa material and then subjected to air drying conditions effective to induce, promote, and/or facilitate self-assembly of collagen fibers contained in the material and entrain at least one bioactive agent in the solidified submucosa material. In these aspects, the amount of air drying time can vary from a few seconds to several days. A suitable air drying time can depend on a number of factors including but not limited to one or more properties of the embolic body, the flowable ECM material, and/or the air drying technique used, as well as the extent or degree of collagen re-assembly desired. In this regard, different combinations of such factors can be developed through routine experimentation so as to provide a coated embolization device having suitable characteristics for a particular application. For example, assembly times can be varied by adjusting the temperature of the air. Again, the flowable ECM materials useful in some forms of the invention will typically be effective to self-assemble at elevated temperatures, for example, at about 37° C. Accordingly, in certain embodiments, reconstituted ECM coating layers are formed, at least in part, by subjecting flowable ECM coating layers to such elevated temperatures, and in certain aspects, placing the device in an incubator.

It is advantageous in some aspects of the invention to perform drying and/or other manufacturing operations under relatively mild temperature exposure conditions that minimize deleterious effects upon any ECM materials being used, for example, native collagen structures and potentially bioactive substances present. Thus, manufacturing operations conducted with no or substantially no duration of exposure to temperatures above human body temperature or slightly higher, say, no higher than about 38° C., will preferably be used in some forms of the present invention. These include, for example, forced air drying at less than about 38° C., or with no active heating—at about room temperature (about 25° C.) or with cooling. Relatively low temperature conditions also, of course, include lyophilization conditions.

Turning now to a discussion of particular drying techniques that can be useful in certain embodiments of the invention, drying by evaporation, or air drying, generally comprises drying a partially or completely hydrated material by allowing the hydrant to evaporate from the material. Evaporative cooling can be enhanced in a number of ways, such as by placing the material in a vacuum, by moving, e.g., blowing, air over the material, by increasing the temperature of the material, by applying a blotting material during evaporation, or by any other suitable means or any suitable combination thereof.

It should be noted that the amount of void space or open matrix structure within an ECM material that has been dried by evaporation is typically more diminished than, for example, an ECM material dried by lyophilization as described below. Accordingly, air drying an ECM material layer is advantageous in some forms of the invention, in that it can provide a dried ECM material layer that is comparatively more collapsed and thinner than a layer dried by a different drying technique, for example, by lyophilization. Such thinner layers are desirable in certain aspects of the invention, because, inter alia, they allow one or more layers to be formed in tight spaces, e.g., between adjacent turns in a microcoil, and/or they enable a greater number of individual layers to be formed within a device coating having a given overall thickness.

Nonetheless, when forming a coating layer of the present invention (including a multilayered coating), the coating layer(s) should be formed in a manner that does not adversely affect the desired physical or other characteristics of the coated embolization product being formed. For example, in certain aspects, one or more coating layers are immobilized on an embolic body so that the one or more properties of the body (e.g., its flexibility, shape memory, etc.) are maintained within a desired, predetermined range. In other aspects, the addition of one or more coating layers to an embolic body brings the flexibility and/or shape memory of the coated device into a desired, predetermined range.

In some embodiments, a dried or substantially dried, collagenous ECM coating layer is subjected to additional mechanical, chemical or other processing to alter one or more of its properties, for example, to make it thinner and denser. Illustratively, such additional processing can include subjecting a coated device of the invention to a suitable ion implantation step. Such techniques can be effective to compact a collagenous coating layer by about 1.5 to about 65 times its initial thickness. An ion implantation step can be performed after the application of any of the coating layers described herein, e.g., after the application of a layer dried via lyophilization. Ion implantation can be used to enhance the adhesion of a remodelable collagenous ECM material to an embolic coil surface, while enabling the coated coil to maintain desired performance and other characteristics such as but not limited to desired flexibility, size, and coil shape memory. Nanoscale surface aberrations which can be left by collided ions of an ion implantation process can also alter certain surface characteristics of a coated device, which in turn can enhance the thrombogenicity of the device, as well as its ability to promote and/or facilitate endothelial cellular migration and cellular adhesion.

Further, it should be noted that remodelable ECM materials having a relatively more open matrix structure (i.e., higher porosity) are capable of exhibiting different material properties than those having a relatively more closed or collapsed matrix structure. For example, an ECM material having a relatively higher porosity is generally softer and more compliant than one having a relatively lower porosity. Also, the rate and amount of tissue growth in and/or around a remodelable material can increase as the amount of open space available in the material's matrix structure for the infusion and support of a patient's cell building components, such as fibroblasts, increases. Therefore, an open matrix structure can provide for quicker, and potentially more, growth of patient tissue in and/or around the remodelable material, which in turn, can lead to quicker remodeling of the material by patient tissue and quicker formation of a desirable embolus. In certain aspects, a layered device coating is provided having a suitable degree of porosity to promote cellular invasion and/or ingrowth, yet is sufficiently compact to provide a coated embolization device possessing suitable performance and other characteristics for a particular application.

A lyophilization process can include providing an ECM material that contains a sufficient amount of hydrant such that the voids in the material matrix are filled with the hydrant. The hydrant can comprise any suitable hydrant known in the art, such as purified water, sterile saline, any of the hydrants contained in the flowable materials described elsewhere herein, or any suitable combination thereof. Illustratively, a flowable material can be placed in a freezer until the material including the hydrant is substantially in a frozen or solid state. Thereafter, the frozen material including the frozen hydrant can be placed in a vacuum chamber and a vacuum initiated. Once at a sufficient vacuum, as is known in the art, the frozen hydrant will sublime from the material, thereby resulting in a dry ECM material.

In other embodiments, a hydrated ECM material can be lyophilized without a pre-freezing step. In these embodiments, a strong vacuum can be applied to the hydrated material to result in rapid evaporative cooling which freezes the hydrant within the ECM material. Thereafter, the frozen hydrant can sublime from the material thereby drying the ECM material. In certain aspects, an ECM material that is dried via lyophilization maintains a substantial amount of the void space, or open matrix structure, that is characteristic of the harvested ECM material.

Device coatings of the invention can comprise any suitable number of layers of material, and any of these layers can possess any of the physical, biological, or other properties of the coating materials described herein. For example, in certain aspects of the invention involving multilayered coatings, at least two of the material layers have different properties. Illustratively, an inner coating layer can be formed from a material that is less dense than material used to form an outer coating layer. A less dense ECM material for forming the inner coating layer (or set of inner coating layers) is advantageous in certain embodiments of the invention, because it is better able to penetrate or flow into crevices, cracks, holes, or other similar spaces on the embolic body surface (whether naturally occurring or man made), compared to a denser material. In one embodiment, one or more inner coating layers are formed using an ECM material having a concentration in a suitable liquid medium of about 2 mg/mL to about 20 mg/mL, more typically from about 4 mg/mL to about 12 mg/mL, while one or more outer coating layers are formed using an ECM material having a concentration in a suitable liquid medium of about 20 mg/mL to about 200 mg/mL, more typically from about 50 mg/mL to about 100 mg/mL.

Similarly, any individual layer in a multilayered coating of the invention can be formed according to any of the processes described herein. Illustratively, a "dip-dry-repeat" process can be employed to form a multilayered coating, wherein at least one layer is air dried and at least one other layer is lyophilized. In any event, different combinations of manufacturing processes and individual layer properties can be developed through routine experimentation so as to provide a coated embolization device having suitable characteristics (e.g., flexibility, shape upon deployment, etc.) for a particular application. In certain aspects, a coating is applied to a starting device so that the coated device is not significantly more stiff than the starting device, for example, not more than about 50% more stiff, more typically not more than about 25% more stiff, and even more typically not more than about 2% to about 10% more stiff than the starting device. Also, in some forms, outer regions of a coating layer comprise an ECM material, while inner regions of the coating layer comprise a non-ECM material. For example, one or more inner layers can comprise an adhesive material and/or a synthetic polymeric material, and one or more outer layers can comprise an ECM material such as porcine SIS.

In addition or as an alternative to air drying, a reconstitution step of the invention can include introducing an embolic body at least partially coated with an amount of a flowable ECM material into a liquid medium. Any suitable liquid medium and any suitable means for introducing the coated device into the liquid medium may be used in this regard. Also, the flowable ECM material can be in contact with the liquid medium for any amount of time to suitably form a reconstituted collagenous material layer coating immobilized on the embolic body surface in accordance with the present invention, e.g., one having a network of self-assembled collagen fibrils, and entraining at least one bioactive agent in the ECM material. Such a network, in some instances, may be generally homogeneous. In certain aspects, this contact time is varied to manipulate one or more characteristics of the reconstituted ECM coating layer formed, for example, the layer's thickness. In some forms, an ECM material layer, before, during, and/or after being reconstituted, is crosslinked by any of the methods disclosed herein.

In certain embodiments, the liquid medium is effective to induce self-assembly of the collagen fibers (e.g., induce fibrillogenesis), and thereafter facilitate and/or promote self-assembly of the collagen fibers without having to add other materials to and/or otherwise manipulate the system, for example, without having to alter the temperature and/or pH of the system. (In this context, the term "system" refers to at least the combination including the embolic body, the coating material, and the liquid medium.) In these embodiments, the contact time between the flowable ECM material and the liquid medium can be from a fraction of a second to several days. A suitable contact time to form a reconstituted ECM coating layer in accordance with the present invention can depend on a number of factors including but not limited to one or more properties of the embolic body, the flowable ECM material, and/or the liquid medium used, as well as the extent or degree of collagen self-assembly desired. In this regard, different combinations of such factors can be developed through routine experimentation so as to provide a coated embolization device having suitable characteristics for a particular application.

In one illustrative embodiment, an amount of flowable submucosa is applied to a surface of an embolic coil, for example by dip coating, and the at least partially coated coil is introduced into a buffered aqueous medium to form a coated embolization device in accordance with the present invention. Any suitable buffered aqueous medium may be utilized in this regard, and advantageously, a buffered aqueous medium will be selected so as not to leave a toxic residue on or within the embolization product formed, and to have a physiological ion concentration and the capacity to hold physiological pH. Suitable buffered aqueous mediums for such purposes may include any of the buffers previously disclosed for preparing a suitable starting ECM gel material, e.g., PBS, HEPES, and DMEM. Also, other suitable media can be used and, if desired, rinsed or otherwise processed to remove any undesired residues from the coatings formed.

In another illustrative embodiment, an embolic device that is at least partially coated with a suitable ECM gel is introduced into a buffer bath to form a coated embolization device in accordance with the present invention. In general, portions of the ECM gel will have already undergone a certain amount of fibrillogenesis. Accordingly, introducing such a gel coating into a buffer bath or other suitable liquid medium will further the fibrillogenesis and matrix assembly, leading to a reconstituted ECM coating layer in accordance with the present invention. In certain aspects, a multilayer coated device is formed by repeating a coating-reconstitution process one or more times.

In other forms, the liquid medium (at least as initially provided) is not configured to induce self-assembly of the collagen fibers (or at least not to the extent of the liquid mediums described above). In such embodiments, self-assembly of the collagen fibers is induced and carried out by further manipulating the system, for example, by adding other materials to the system and/or altering certain properties of the system such as but not limited to its temperature, pH, and/or the like. For example, it should be noted that solubilized ECM material will typically be effective to self-assemble at elevated temperatures, for example, at about 37° C. Accordingly, in certain embodiments, a reconstituted ECM coating layer in accordance with the present invention can be formed by placing a solubilized ECM coating layer in a liquid medium, and thereafter suitably raising the temperature of the system to allow or cause the collagen fibers to self-assemble. In this regard, reconstitution times can be varied by adjusting the temperature of the liquid medium utilized. In certain aspects, a flowable ECM material is reconstituted under gravitational force of less than one gravity, preferably about zero gravity.

As previously mentioned, reconstituted ECM coating layers of the present invention are formed in a way that allows them to retain one or more native bioactive substances (such as those described above) in their ECM material. Nonetheless, in certain embodiments, one or more additional bioactive agents, whether or not native to the source of the ECM tissue material, can also be incorporated into and/or onto the ECM material before, during, and/or after a reconstitution step. For example, any of the non-native bioactive agents previously described (e.g., proteins, carbohydrates, growth factors, therapeutics, nucleic acids, cells, pharmaceuticals, and the like) can be added to the starting material before the reconstituted coating layer is formed, or alternatively, can be disposed on the reconstituted ECM coating layer after it is formed. In certain embodiments, such additional components are added to an ECM starting material that is turned from an aqueous ungelled composition into a gel. This may be accomplished, for example, by forming a dry mixture of a powdered ECM hydrolysate with the additional component(s), and then gelling the mixture, or by incorporating the additional component(s) into an aqueous, ungelled composition of the ECM hydrolysate before, during (e.g. with), and/or after addition of the neutralization agent. The additional component(s) can also be added to the formed ECM gel, e.g., by infusing or mixing the component(s) into the gel and/or coating them onto the gel.

In certain preferred aspects, coated embolization products of the invention are adapted to additionally serve as substrates and/or scaffolds in the delivery of therapeutics, etc. to patients. For example, an antineoplastic agent such as but not limited to doxorubicin can be added to a coated device of the invention. Such drugs or other bioactive agents can be bound to or otherwise associated with the matrix in any suitable fashion, e.g., stored on the collagen fibers of the network and/or within the pores of the matrix. In certain aspects, incorporation of a drug into a product of the invention includes suitably contacted an ECM coating layer with the drug. This can be achieved by spraying, soaking, or otherwise contacting the ECM material with an aqueous solution of the drug or other bioactive agent for a period of time suitable to incorporate a desired amount of the drug. This contact time may vary, for example, from a few seconds to several days, depending upon the circumstances.

In addition to dip coating, the various coating starting materials described herein can be disposed on, applied to, etc. an embolic body surface in any suitable manner including but not limited to by spray coating, wiping, vapor deposition, various electrophoretic techniques, vacuum deposition, electrospinning, and the like.

Illustratively, an ECM material can be coated onto a surface of an embolic body using an electrophoretic technique. Such an electrophoretic technique may be accomplished, for example, in a solution containing ECM material and with a metallic coil device as the cathode, at a potential, e.g., of about two to four volts. Illustratively, a fluid composition can include a solubilized or suspended collagenous ECM material in an acidic solution. The acid imparts a positive charge to protein components of the ECM material, and allows it to travel in an electrical field. By attaching a metal object to the negative electrode of a power source, and then immersing both the positive and negative electrodes in the acidic fluid composition, a layer of collagenous ECM material can form on the negatively charged embolic device surface, forming a coated embolization device.

Coated embolization devices of the invention find wide use in the diagnosis, treatment, and follow-up of various medical conditions. Illustratively, an inventive coated device can be used to occlude or substantially occlude a lumen or other open space in a patient's body, especially within the vasculature. In certain aspects, one or more coated devices of the invention are implanted within a particular blood vessel to block the blood vessel, deprive a certain area of life-sustaining blood, or fill a cavernous area in the blood vessel, e.g., an aneurysm sac stemming from an artery. Examples of medical conditions that can be treated with devices of the invention include but are not limited to uncontrolled vascular bleeding (such as menorrhagia), ruptured and unruptured vascular aneurysms (such as thoracic aortic aneurysm, abdominal aortic aneurysms, cerebral aneurysms), benign tumor growth (such as uterine fibroids), malignant tumor growth (particularly hepatic, renal and other solid tumors), and vascular malformations (AV malformations, vascular tumors). Coated embolization devices of the invention can also be useful in medical procedures to provide contraception.

In certain other embodiments, a product including coated embolic particles is implanted within a patient's body. For example, such a product can be implanted within (e.g., injected into) the vascular system, perhaps within, on, or around a vascular vessel in need of treatment. Illustratively, when such a product (e.g., a suitable liquid carrier such as a gel material carrying the coated embolic particles) having a suitable viscosity is injected into the lumen of an aneurysm, the product will generally stay in the lumen and provide therapeutic benefit to the aneurysm, e.g., to partially or fully cause occlusion of the vessel, to cause emboli formation, or to pack (or fill) an aneurysm lumen. As an embolization or aneurysm lumen filling device, particulate-containing products of the invention are particularly advantageous in that they promote healing of the occluded area and healing of the aneurysm. In preferred aspects, a particulate gel product including one or more drugs is injected into, on, or around a tumor as part of a chemoembolization procedure or method.

The inventive coated embolization devices described herein may be delivered to a treatment site in any suitable manner. Illustratively, an embolic device, e.g., a coil, may be placed within the distal end of a translumenally advanceable delivery device having a cannula (e.g., a catheter), and when the distal end of the device is properly positioned, the coil may be pushed out of the end of the device with, for example, a guidewire, to release the coil at the desired location. This placement procedure can be conducted under fluoroscopic visualization or using other suitable visualization techniques such that the movement of the coil may be monitored and the coil may be placed at a desired location. In certain aspects, an embolization device is made radiopaque by a suitable procedure. In this regard, any radiopaque substance, including but not limited to, tantalum such as tantalum powder, can be incorporated into the device. Other radiopaque materials comprise bismuth, iodine, and barium, as well as other suitable markers.

The coated embolization devices of the invention can be modified before, during, and/or after deployment. Illustratively, a device may be reshaped, sterilized, and/or treated (e.g., brought into contact, impregnated, coated, etc.) with one or more desirable compositions, such as any of those previously disclosed herein, e.g., anticoagulants (e.g., heparin), growth factors or other desirable property modifiers. In certain aspects, before, during, and/or after deployment of a device in accordance with the present invention, one or more portions of the device are reshaped or removed.

In addition to or as an alternative to any of those previously described (e.g., the incorporation of one or more non-native bioactive components), other forms of manipulation and/or processing can be performed on devices that have already been coated in accordance with the invention. For example, one or more thrombogenic components that are configured to enhance the overall thrombogenicity and/or surface area of the embolic body can be incorporated into a coated product. Illustratively, one or more threads or fibers in various configurations, e.g., tufted, looping, braided, etc., may be attached to or otherwise associated with a device after it is coated. Other suitable thrombogenic components include mesh and film materials, various particulates, strands, filaments, windings, twisted elements, and expandable elements. Of course, such thrombogenic components can also be incorporated into a product before it is coated in accordance with the present invention and/or during and/or after the application of any coating layer.

The coating processes described herein can be used to coat existing embolization devices. In this regard, embolic bodies that are suitable for coating in accordance with the present invention may or may not already be coated or partially coated with another substance. If already coated, these existing coating substances may be similar to or different than the coating materials to be added. In some forms, an ECM coating material is applied on top of a non-ECM coating material.

Regardless of whether the embolic body is already coated and regardless of any other physical, chemical, biological, or other characteristic of the to-be-coated device, it will be understood that an embolic body such as any of those discussed herein, prior to being coated in accordance with the present invention, may or may not receive some form of surface pre-treatment or conditioning to modify one or more characteristics of the device, or any portion thereof. Although not necessary to broader aspects of the invention, such a modification step can be performed prior to (or as part of) any processing step of the invention, for example, between the application of successive individual coating layers to a device. As described more thoroughly below, a suitable modification step can involve the addition or removal of material from an embolic body surface.

Such pre-treatment may be desirable or even necessary in some forms of the invention, for example, where a particular embolic body surface (i.e., a coated or uncoated surface) and coating material are undesirable in terms of being able to satisfactorily adhere to one another. For example, such conditioning can be used to physically, chemically, or otherwise alter the surface characteristics of the embolic body to promote and/or facilitate adhesion of the coating material to the surface and/or to try to ensure that a continuous layer of material is formed along the surface.

Suitable methods for surface treatment include but are not limited to physical, chemical, and electrochemical techniques such as but not limited to chemical etching, sputtering, pressurized grit etching, and plasma etching. Surface modification with physical techniques can be achieved with abrasives, such as found in sand blasting which produces macroporous surfaces, or machining with equipment, such as milling machines that also produce macro pores. Heat treatment of surfaces is another physical alteration method, which can be used, for example, anneal, harden and/or smooth metals. In some forms, material is added to an embolic body surface to create asperities on the surface. Illustratively, a metallic powder can be disposed on a metallic embolic body surface by rolling the embolic body in the powdered material or by spraying the powdered material onto surfaces of the embolic body. The metallic body can be electrostatically charged to a polarity opposite that of the powdered material to enhance adhesion between the two. The particle-coated body can then be heated in a manner that welds the particles to the metal, yet does not undesirably alter the form of the body. Other modes of adding material to an embolic body surface include but are not limited to sputtering using an ion beam and deposition of hydroxyapatite.

Processes for chemically modifying metallic surfaces can include but are not limited to acid or base etching, "pickling," and electrochemical passivation. However, it should be noted that certain chemicals may be undesirable for use in conjunction with remodelable materials, because leftover quantities of such chemicals and/or byproducts of chemical processes can diminish or even destroy the remodelable properties of a remodelable coating material. Therefore, where preservation of remodelable properties is desired, any chemical modification of the embolic body can be performed to an extent or in a fashion that allows the later coated material to retain at least a portion of its remodelable properties. Illustratively, a chemically treated device may be rinsed with water or otherwise suitably treated to remove any residual chemicals and/or byproducts prior to being coated.

Chemicals useful in this aspect of the invention can include any acid or base that cleans and/or degrades, removes, and/or otherwise suitably modifies portions of a metal or alloy surface. Such chemicals can include but are not limited to nitric acid, hydrochloric acid, sulfuric acid, and sodium hydroxide. These and other suitable chemicals can be sprayed onto or used to soak the embolic body, and then rinsed off the surface after a predetermined amount of time. The length of time the chemical is left on the surface can depend on the etch rate and the depth of etch desired. Thus, techniques and mediums known in the art for completely removing metallic coatings can be used for relatively shorter periods of time to suitably modify metallic surfaces in accordance with the present invention. In some forms, chemical treatment is performed to remove impurities such as but not limited to grease, dirt, a hydroxide layer, etc., from the embolic body surface. In some aspects, chemical treatment is performed to entirely remove a surface layer from the embolic body, for example, a surface layer including oxidized platinum.

Illustratively, polymer chemical surface modifications can include cleaning procedures with aqueous and/or organic solvents, while suitable machining techniques and/or heat treatment can also be used to modify polymeric surfaces. Also, electrochemical surface modification can include electroplating of materials such as nickel, copper, chrome, titanium, precious metals and/or other commonly used plating metal and metallic compounds. Other surface treatments include conventional coating techniques (e.g., spray painting, dipping, etc.) as well as vapor deposition and plasma grafting technologies. Useful plasma applications can include the treatment of solid surfaces, deposition of films, surface modifications and/or dry etching of surface layers.

In certain aspects of the invention, reconstituted or otherwise reassembled ECM coating materials of the invention are subjected to a crosslinking process. Suitable crosslinking techniques for this aspect of the invention include but are not limited to photo-crosslinking, chemical crosslinking, and protein crosslinking induced by dehydration or other means. Illustratively, a remodelable ECM coating material can be crosslinked internally within a single coating layer, and/or crosslinking may be used in whole or in part to enhance bonding between multiple ECM coating layers. Nonetheless, because certain crosslinking techniques, certain crosslinking agents, and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties.

In some embodiments, coated embolization devices of the invention can incorporate an effective amount of one or more antimicrobial agents or agents otherwise useful to inhibit the population of the device or surrounding tissue with bacteria or other deleterious microorganisms. Illustrative such agents can include, for example, silver compounds, such as silver salts (e.g. silver sulfate), dextran, chitosan, chlorhexidine, and/or nitric oxide donor compounds. In illustrative embodiments, such agents can be incorporated throughout the devices and/or on surfaces and/or selected regions thereof. These or other similar therapeutic agents can be incorporated directly on or in the devices of the invention, or they can be incorporated with a suitable binder or carrier material, including for instance hydrogel materials.

The present invention also provides, in certain aspects, a line of medical products, wherein a medical product of the invention includes one or more coated embolization devices of the invention in a sealed package. When a plurality of devices is included, the devices can each be of substantially the same size and shape, or, alternatively, can vary with respect to size and shape.

In some forms of the invention, medical products are provided that include one or more coated embolization devices such as any of those described herein, and potentially also a suitable delivery device, enclosed within sterile medical packaging. Illustratively, such a medical product can have packaging including a backing layer and a front film layer that are joined by a boundary of pressure-adhesive as is conventional in medical packaging, wherein the contents of the packaging are sealed between the backing layer and front film layer.

Sterilization of such a medical product may be achieved, for example, by irradiation, ethylene oxide gas, or any other suitable sterilization technique, and the materials and other properties of the medical packaging will be selected accordingly. Also, coated embolization devices of the invention can be contained in a sterile packaging in any suitable state. Suitable states include, for example, a hydrated or dehydrated state. The devices can be dehydrated by any means known in the art (e.g., lyophilization or air dried). If biotropic ECM coated devices of the present invention are stored in a dehydrated state, it is preferred that they retain all of its biological and mechanical properties (e.g., shape, density, flexibility, etc.) upon rehydration.

Additionally, the package can include indicia to communicate the contents of the package to a person, machine, computer, and/or electronic device. Such indicia may include the dimensions of, the type of materials used to form, and/or the physical state of, the contents of the package. In certain embodiments, the embolization devices are packaged for sale with instructions for use. For example, in certain preferred embodiments, a medical product includes at least one embolization device sealed within a sterile package, wherein the packaging can have visible indicia identifying the at least one device as a vascular occlusion device, and/or can contain or otherwise be associated with printed materials identifying the contents as a vascular occlusion device or other suitable occlusive device and including information concerning its use as such a device. The packaging could also include visible indicia relating to the dimension of the at least one device, and/or relating to the vessel diameter(s) or other open spaces for which the at least one device is configured.

In order to promote a further understanding of the present invention and its features and advantages, the following specific examples are provided. However, it will be understood that these examples are illustrative and are not limiting of the invention.

At some point in each of the experiments described in the following examples, an SIS digest material was utilized. This base digest material, which can be formed as described directly below, was used in forming both the "low concentration" (10.0 mg SIS/ml HCl) and "high concentration" (66.7 mg SIS/ml HCl) SIS gels described.

Formation of Base SIS Digest Material

Powdered (produced by cryogrinding isolated/washed but non-disinfected) porcine small intestinal submucosa was frozen in a −80° C. freezer. Then, the frozen SIS powder was removed from the freezer and centrifuged at 7000 rpm for 30 minutes to obtain an SIS paste. This SIS paste was placed in a container with a solution of HCl (50-60 grams of SIS per L of HP water used; 10 mL of 1N HCl per L of HP water used). Pepsin was then added to the container (1 gram of pepsin per L of HP water used), and the paste was allowed to digest for 48-72 hours with constant stirring. This digest was then centrifuged at 15,000 rpm for 45 minutes at 4° C. After removing the supernatant, the solids of the digest were lyophilized. 100 mg of this lyophilate was then added to 1.5 mL of 0.01 M HCl, and placed in a dialysis tube (3500 MW cut off). The filled tube was placed in cylindrical jar containing 0.2% PAA (peracetic acid) for 2 hours. The PAA-treated digest was then dialysed against 0.01 M HCl for at least 48 hours to obtain the SIS digest material.

Example 1

An SIS digest material produced in the general manner as described above (but having a concentration of 10.0 mg SIS/ml HCl) was used to form a "low concentration" SIS gel. Two milliliters of this low concentration SIS gel, 135 µl 0.25 M NaOH, and 240 µl 10×PBS were mixed using two 5 mL syringes. After measuring the pH of the gel to ensure neutralization (7.5-8.0 is suitable), a platinum coil (having a diameter of 340 µm or 400 µm) was dipped in the gel and optionally reimmersed several times to coat the coil. The SIS-coated coil was then incubated at 37° C. for 45 minutes, and air dried in a laminar flow hood for 1 hour.

Example 2

A platinum coil (having a diameter of 340 µm or 400 µm) was sonicated in 2 M $H_2SO_4$ for 15 minutes. Then, the coil was rinsed three times in a beaker of high purity (HP) water by soaking for one minute and changing the water between rinses. Thereafter, the coil was coated as described in Example 1.

Example 3

A platinum coil (having a diameter of 340 µm or 400 µm) was sonicated in 0.1 M NaOH for 15 minutes. Then, the coil was rinsed three times in a beaker of HP water by soaking for one minute and changing the water between rinses. Thereafter, the coil was coated as described in Example 1.

Example 4

A platinum coil (having a diameter of 340 µm or 400 µm) was sonicated in 2 M $H_2SO_4$ for 15 minutes. Then, the coil was rinsed three times in a beaker of high purity (HP) water by soaking for one minute and changing the water between rinses. Thereafter, the coil was coated three separate times as described in Example 1, i.e., allowing the previous coat to dry before applying the next coat.

Example 5

An SIS digest material produced in the general manner described above (but having a concentration of 10.0 mg SIS/ml HCl) was used to form a "low concentration" SIS gel. Also, another SIS digest material produced in the general manner described above (but having a concentration of 66.7 mg SIS/ml HCl) was used to form a "high concentration" SIS gel.

A platinum coil (having a diameter of 340 µm or 400 µm) was sonicated in 2 M $H_2SO_4$ for 15 minutes. Then, the coil was rinsed three times in a beaker of high purity (HP) water by soaking for one minute and changing the water between rinses. Thereafter, the coil was coated twice as described in Example 1, i.e., using the low concentration SIS gel and allowing the first coat to dry before applying the second coat.

Following the low concentration gel coatings, two milliliters of the high concentration SIS gel, 205-210 µl 0.25 M NaOH, and 245 µl 10×PBS were mixed using two 5 mL syringes. After measuring the pH of the gel to ensure neutralization (7.5-8.0 is suitable), a platinum coil (having a diameter of 340 µm or 400 µm) was dipped in the gel and optionally re-immersed several times to coat the coil. The SIS-coated coil was then incubated at 37° C. for 45 minutes, and air dried in a laminar flow hood for 1 hour. This high concentration gel coating process was repeated two more times, i.e., allowing the previous coat to dry before applying the next coat. In all, the coil received five separate coatings (2 low concentration coatings and 3 high concentration coatings). Coated coils produced in this manner were terminally sterilized using either EtO or e-beam.

Example 6

A coated coil was prepared as described in Example 5, except that the coil received a total of ten separate coatings (2 low concentration coatings as described and 8 high concentration coatings as described). Coated coils produced in this manner were terminally sterilized using either EtO or e-beam.

Example 7

A coated coil was prepared as described in Example 5, except that the coil received a total of fifteen separate coatings (2 low concentration coatings as described and 13 high concentration coatings as described). Coated coils produced in this manner were terminally sterilized using either EtO or e-beam.

Example 8

A coated coil was prepared as described in Example 5, except that the coil received a total of twenty separate coatings (2 low concentration coatings as described and 18 high concentration coatings as described).

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. An embolization device, comprising:
   an embolic body having an elongate primary coil element, the elongate primary coil element having a wire coil about a first axis providing adjacent coil turns that abut one another defining grooves between the adjacent coil turns occurring between adjacent peaks of the coil turns, and wherein the elongate primary coil element is in the shape of a secondary coil about a second axis; and
   a coating material immobilized on a surface of said embolic body, said coating material comprising a biotropic extracellular matrix gel, said biotropic extracellular matrix gel comprising a network of self-assembled collagen fibrils and at least one bioactive agent retained in the extracellular matrix gel, the bioactive agent selected from the group consisting of a proteoglycan, a growth factor, a glycoprotein, and a glycosaminoglycan, and wherein said coating material has a greater thickness over said grooves than over said peaks.

2. The device of claim 1, wherein said network of self-assembled collagen fibrils is generally homogeneous.

3. The device of claim 1, wherein said coating material is dried.

4. The device of claim 1, wherein said coating material comprises a single layer of biotropic extracellular matrix gel.

5. The device of claim 1, wherein said coating material comprises two to six layers of biotropic extracellular matrix gel.

6. The device of claim 1, wherein said coating material further comprises at least one additional bioactive agent selected from the group consisting of a growth factor, a protein, a proteoglycan, a glycosaminoglycan, a physiologically compatible mineral, an antibiotic, a chemotherapeutic agent, a pharmaceutical, an enzyme, a hormone, and genetic material.

7. The device of claim 1, wherein coating material has a thickness of 0.5 to 30 μm.

8. The device of claim 1, wherein coating material has a thickness of 0.5 to 12 μm.

9. The device of claim 1, wherein said embolization device is not more than 50% stiffer than said embolic body.

10. The device of claim 1, wherein said embolization device is not more than 10% stiffer than said embolic body.

11. The device of claim 1, wherein said embolic body comprises a metal.

12. The device of claim 1, wherein said embolic body comprises a synthetic polymeric material.

13. The device of claim 1, wherein said coating material surrounds and covers the entire embolic body.

14. The device of claim 1, wherein said network of self-assembled collagen fibrils is porous so as to provide an open matrix of pores into which new patent tissue can grow following implantation of the embolization device in the body of a patient.

15. The device of claim 3 enclosed within sterile packaging, wherein said biotropic extracellular matrix gel has a nucleic acid level of less than 2 μg/mg.

16. An embolization device, comprising:
    an embolic body; and
    a multilayered coating comprising at least two individual material layers, said multilayer coating including a reassembled extracellular matrix gel layer formed over a surface of the embolic body so as to provide a coating layer over said surface, wherein the reassembled extracellular matrix gel layer comprises a network of self-assembled collagen fibrils and at least one bioactive agent retained in the reassembled extracellular matrix gel layer, the bioactive agent selected from the group consisting of a proteoglycan, a growth factor, a glycoprotein, and a glyco saminoglycan;
    wherein said embolic body comprises an elongate primary coil element, the elongate primary coil element having a wire coil about a first axis, wherein the elongate primary coil element is in the shape of a secondary coil about a second axis providing adjacent coil turns that abut one another, defining grooves between the adjacent coil turns, and wherein said multilayered coating has a greater thickness in said grooves.

17. The embolization device of claim 16, wherein said network of self-assembled collagen fibrils is generally homogeneous.

18. The embolization device of claim 16 wherein, said multilayered coating includes more than one reassembled extracellular matrix gel layer but less than twenty reassembled extracellular matrix gel layers.

19. The embolization device of claim 18, wherein said multilayered coating includes an air dried extracellular matrix gel layer and a lyophilized extracellular matrix gel layer.

20. The embolization device of claim 18, wherein said multilayered coating has a thickness of 0.5 to 30 μm.

* * * * *